US012144969B1

(12) United States Patent
Fogg et al.

(10) Patent No.: US 12,144,969 B1
(45) Date of Patent: Nov. 19, 2024

(54) ATTACHMENT MECHANISM, MODULE AND ASSEMBLY HEREWITH

(71) Applicant: Sanofi, Paris (FR)

(72) Inventors: Oliver Fogg, Bristol (GB); Michael Jugl, Frankfurt am Main (DE); Martin Vitt, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/590,727

(22) Filed: Feb. 28, 2024

(51) Int. Cl.
*A61M 5/31* (2006.01)
*A61M 5/315* (2006.01)

(52) U.S. Cl.
CPC .......... *A61M 5/31* (2013.01); *A61M 5/31548* (2013.01); *A61M 2205/581* (2013.01)

(58) Field of Classification Search
CPC .......... A61M 5/31548; A61M 5/31533; A61M 5/3155; A61M 5/31551; A61M 5/31553; A61M 2005/3125; A61M 2005/3126
See application file for complete search history.

(56) References Cited

U.S. PATENT DOCUMENTS

| | | | |
|---|---|---|---|
| 5,693,027 | A | 12/1997 | Hansen et al. |
| 6,663,602 | B2 | 12/2003 | Moller |
| 7,241,278 | B2 | 7/2007 | Moller |
| 9,937,294 | B2 | 4/2018 | Quinn et al. |
| 2001/0047153 | A1 | 11/2001 | Trocki et al. |
| 2008/0306446 | A1 | 12/2008 | Markussen |
| 2009/0054839 | A1 | 2/2009 | Moller et al. |
| 2018/0154086 | A1 | 6/2018 | Toporek et al. |
| 2018/0361072 | A1* | 12/2018 | Streit .................. A61M 5/3158 |
| 2019/0366006 | A1* | 12/2019 | Hewson ............ A61M 5/31526 |
| 2021/0369973 | A1* | 12/2021 | Byerly .............. A61M 5/31551 |

(Continued)

FOREIGN PATENT DOCUMENTS

| | | |
|---|---|---|
| EP | 1570876 B1 | 12/2009 |
| EP | 2814547 B1 | 7/2015 |
| EP | 2890434 B1 | 4/2020 |

(Continued)

OTHER PUBLICATIONS

Hamers-Casterman et al., "Naturally occurring antibodies devoid of light chains," Nature, Jun. 3, 1993, 363(6428):446-448.

(Continued)

*Primary Examiner* — Dung T Ulsh
(74) *Attorney, Agent, or Firm* — Fish & Richardson P.C.

(57) ABSTRACT

The present disclosure is generally directed to an attachment mechanism suitable for attaching for example a module to an object that is cylindrical or polygonal in cross section, e.g. to a portion of a drug delivery device. Further, the disclosure is directed to an electronic system, e.g. an electronic add-on module, which is configured to be, e.g. releasably, attached to a drug delivery device as well as an assembly comprising the electronic add-on module as well as the drug delivery device. The attachment mechanism may comprise a housing, a gripping portion with an elastically deformable sleeve and an actuator for operating the gripping portion between an open condition and a clamping condition. The actuator is configured to be operated to rotate the distal end and the proximal end of the sleeve relative to each other, thereby operating the gripping portion between the open condition and the clamping condition.

20 Claims, 2 Drawing Sheets

(56) References Cited

U.S. PATENT DOCUMENTS

2022/0016352 A1   1/2022   Jugl et al.

FOREIGN PATENT DOCUMENTS

| WO | WO 2004/068820 A2 | 8/2004 |
| WO | WO 2004/078239 A1 | 9/2004 |
| WO | WO 2005/018629 A1 | 3/2005 |
| WO | WO 2005/018721 A1 | 3/2005 |
| WO | WO 2006/003388 A2 | 1/2006 |
| WO | WO 2006/030220 A1 | 3/2006 |
| WO | WO 2009/132777 A1 | 11/2009 |
| WO | WO 2014/033195 A1 | 3/2014 |
| WO | WO 2016/198516 A1 | 12/2016 |
| WO | WO 2019/145415 A1 | 8/2019 |

OTHER PUBLICATIONS

Holt et al., "Domain antibodies: proteins for therapy," Trends in Biotechnology, Nov. 2003, 21(11):484-490.

Muyldermans, "Single domain camel antibodies: current status," Reviews in Molecular Biotechnology, Jun. 2001, 74(4):277-302.

Needle-based injection systems for medical use Requirements and test methods, Part 1: Needle injection systems, ISO 11608-1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 1989, 341(6242):544-546.

* cited by examiner

ATTACHMENT MECHANISM, MODULE AND ASSEMBLY HEREWITH

TECHNICAL FIELD

The present disclosure is generally directed to an attachment mechanism suitable for attaching for example a module to an object that is essentially cylindrical or polygonal in cross-section, e.g. to a portion of a drug delivery device. Further, the disclosure is directed to an electronic system, e.g. an electronic add-on module, which is configured to be, e.g. releasably, attached to a drug delivery device as well as an assembly comprising the electronic add-on module as well as the drug delivery device.

BACKGROUND

Electronic add-on modules may be attached on to a drug delivery device, e.g. a pen-type injection device. Such drug delivery devices often comprise a housing with a container configured to receive a drug or a cartridge filled with a drug, a dose setting unit comprising a dose dial user interface, e.g. a dial grip, at least rotationally moveable with respect to the housing during dose setting and an injection user interface, e.g. a dose button, at least axially moveable with respect to the housing for causing dose dispensing, and a dose delivery unit comprising a plunger at least axially moveable with respect to the housing during dose dispensing.

Electronic add-on modules for releasable attachment to drug delivery devices can be used to measure relevant data with respect to dose setting and/or dose dispensing. Due to the different dimensions and working principles of known injection devices, especially regarding dose dial user interfaces and injection user interfaces, such add-on modules are typically tailored to fit to one specific drug delivery device. This requires providing different modules for different devices.

Electronic add-on modules described in WO 2016/198516 A1 include a sleeve-like portion to be positioned over a dosage knob or dial grip of an injection device. A resilient padding is provided on the inner surface of the sleeve-like portion. The padding deforms to accommodate the dosage knob within the cavity of the sleeve-like portion.

Further, monitoring devices for attachment to an injection device are described in WO 2019/145415 A1. This add-on device comprises a coupling element adapted for accommodating the push button and the selector of an insulin pen. In order to adapt to the specific form of any dose selector, the coupling element comprises a gasket with an inner orifice, whose inner surface is similar to the external surface of the selector, such that it can slide along it and embrace it achieving a firm attachment thereto. By employing different designs for the gasket, the device can be used with any available model of drug pen. The gasket is a removable element which can be detached from the coupling element for example, to be interchanged with other gaskets for the adaptation of the device for its coupling to different models of drug pens.

SUMMARY

The present disclosure describes an improved attachment mechanism, an improved electronic add-on module suitable to be used with various different drug delivery devices and an improved assembly comprising a drug delivery device and such an electronic add-on module.

An attachment mechanism suitable for attaching a module to an object that is essentially cylindrical or polygonal in cross section, like a drug delivery device or a portion thereof, may comprise a housing, a gripping portion and an actuator for operating the gripping portion between an open condition, i.e. a relaxed state or condition of the attachment mechanism permitting attachment or detachment, and a clamping condition, i.e. a resting state or condition in which the module is held and fixed on the object. In other words, the griping portion may be opened and closed by a user for changing between said two conditions.

According to an aspect of the present disclosure, the gripping portion comprises an elastically deformable sleeve with a longitudinal axis, typically the central axis of the sleeve, a distal end and an opposite proximal end which ends are axially (e.g. vertically) constrained, that is the proximal end and the distal end are fixed with respect to each other such that their distance in the direction of the longitudinal axis does not change. The proximal end of the sleeve is (directly or indirectly) coupled to the housing and the distal end of the sleeve is (directly or indirectly) coupled to the actuator. The actuator is configured and designed to be operated in order to rotate the distal end of the sleeve relative to the proximal end of the sleeve, thereby operating the gripping portion between the open condition and the clamping condition. In other words, the gripping portion, more specifically for example the sleeve, can assume various inner diameters. This has the benefit of providing a mechanism e.g. for an add-on module which fits onto different drug delivery devices without requiring individual adapter parts. Rather, the attachment mechanism or a module with such a mechanism is configured to be put, e.g. pressed, onto injectors of varying diameters, for example from around 14 mm to 18 mm, providing secure attachment of the module via a friction fit regardless of the drug delivery device dimensions. The sleeve may be configured to have a holding torque of at least 750 Nmm, e.g. between 1.250 Nmm and 2.500 Nmm or between 1.000 Nmm and 1.500 Nmm, for example about or exactly 1.350 Nmm, when attached to a drug delivery device component having a diameter of about 14 mm to 18 mm and when being in its clamping condition, i.e. when the opposite ends of the sleeve are twisted by at least 15° with respect to each other, e.g. by 20° to 50°, for example by about 35°.

The attachment mechanism of the present disclosure may be a mechanism that allows the attachment of a smart cap device onto dialing members of injector pens of varying geometries and diameters. This is achieved using a flexible, e.g. elastomeric, sleeve which is fastened to the housing which may be a smart cap housing. The proximal (or upper) edge of the sleeve is for example fixed and stationary, while the distal (or lower) edge is attached in such a way that it is allowed to rotate around the longitudinal axis. Alternatively, the distal end may be rotated relative to a stationary proximal end or both ends may rotate relative to each other. This rotation causes the initially cylindrical or conical sleeve to deform inwards, reducing the inner diameter of the closure. When twisted while being constrained axially, the sleeve takes the form of a hyperboloid, whose inner diameter is proportional to the relative rotation angle of the distal end with respect to the proximal end. In other words, this relative rotation causes the sleeve to be either in an open condition with a relatively large inner diameter of the sleeve or in a clamping condition in which the sleeve takes a hyperboloid shape with reduced inner diameter. Thus, according to one aspect of the present disclosure, the dimension, for example the inner diameter, of the sleeve of the gripping portion can be, e.g. elastically, adapted to fit to different dimensions and/or contours of different drug delivery devices, for example of the dose dial user interfaces of the devices.

In one example of the present disclosure, the proximal end of the sleeve of the attachment mechanism is attached to a ring which is movable by means of the actuator. For example, the actuator may comprise at least one spring and an interface that can be manipulated by a user. The at least one spring may be a compression spring acting on the sleeve and the interface may be a push button acting on the compression spring. As an alternative, the at least one spring may be a torsion spring acting on the sleeve and the interface may be a lever acting on the torsion spring. In other words, the at least one spring may be configured to bias and/or hold the sleeve in the clamping position, i.e. the hyperboloid shape of the sleeve, and the interface of the actuator may be configured to switch the mechanism against the bias of the at least one spring into the open condition in which the sleeve is in its substantially cylindrical or conical shape.

The ring may be in toothed or splined engagement with the actuator. For example, the ring may comprise a toothed portion, e.g. a straight or bent toothed rack, and the interface may comprise teeth meshing with this toothed portion such that actuation of the interface causes movement, especially rotation, of the ring attached to the sleeve. In an example of the present disclosure, the actuator, e.g. the interface of the actuator, is configured to be displaced in a plane perpendicular to a longitudinal axis of the sleeve or is configured to be rotated about the longitudinal axis of the sleeve, thereby operating the gripping portion with the sleeve between the open condition and the clamping condition.

According to an independent aspect of the present disclosure, the attachment mechanism or a module with such an attachment mechanism at least consist of the following functional elements: a housing, an elastomeric sleeve with a rotatable ring and a setting/releasing mechanism with an actuator. In an example, the upper edge of the elastomeric sleeve is rigidly attached to the housing, while the lower edge is fixed to the rotatable ring. The ring itself may be attached to the housing in a way that constrains it in the axial direction but allows free rotation about the axis of the sleeve or the module. Twisting the ring causes the sleeve to constrict in the center, forming a hyperboloid shape. The reduction of the inner diameter of the sleeve due to this constriction allows it to make contact and securely grip an injector dial of any diameter. Because the sleeve material is flexible and compliant, it conforms to any arbitrary dial geometry.

The attachment mechanism may be used in or with an electronic add-on module which may be, e.g. releasably, attached to the drug delivery device by frictional, elastic and/or form fit engagement with the releasable gripping portion. A module according to the present disclosure comprises an attachment mechanism as defined above. An assembly according to the present disclosure comprises a drug delivery device and an electronic add-on module configured for releasable attachment to the drug delivery device.

Drug delivery devices may comprise at least a housing with a container configured to receive a drug or a cartridge filled with a drug. Further, the drug delivery device may comprise a dose setting unit and a dose delivery unit. Suitable drug delivery devices to be used with a mechanism or module according to the present disclosure are described e.g. in WO 2004/078239 A1, EP 1 570 876 B1, EP 2 814 547 B1, EP 2 890 434 B1, WO 2005/018721 A1, WO 2009/132777 A1, WO 2014/033195 A1, U.S. Pat. No. 5,693,027 A, 6,663,602 B2, 7,241,278 B2 or 9,937,294 B2. In addition to manually driven devices, the module may be used with spring driven devices as described in US 2008/306446 A1 or US 2009/054839 A1. However, the present disclosure is not limited to these examples of drug delivery devices. Rather, other drug delivery devices with a stationary and/or operable portion having an e.g. substantially cylindrical shape may be used with the module. For example, the drug delivery devices may comprise a user interface for selecting and/or dispensing a fixed or variable dose of a drug.

The dose setting unit may comprise a dose dial user interface, e.g. a dose dial grip, which is, at least rotationally, e.g. helically, moveable with respect to the housing during dose setting and an injection user interface at least axially moveable with respect to the housing for causing dose dispensing. The injection user interface may be a separate component part, e.g. a dose button, which may be displaced relative to the dose dial user interface for causing dose dispensing. As an alternative, the dose dial user interface and the injection user interface may be portions of one single component part, e.g. a combined dose dial and injection knob.

The electronic add-on module may comprise a first portion which comprises the attachment mechanism. The module may further comprise an optional second portion coupled to the first portion allowing relative axial movement parallel to the first longitudinal axis with respect to the first portion. The first portion may define an auxiliary dose dial user interface and may be configured to be releasably attached to the dose dial user interface of the drug delivery device such that the first portion follows the movement of the dose dial user interface and vice versa when attached to the drug delivery device. The second portion may define an auxiliary injection user interface configured to apply pressure onto the injection user interface of the drug delivery device when attached to the drug delivery device.

In an electronic add-on module configured to be releasable attached to a drug delivery device the electronic add-on module may comprise an attachment mechanism as mentioned above configured for releasable attachment to a portion of the drug delivery device, especially but not limited to a dose dial user interface, e.g. a dose dial grip. The electronic add-on module may comprise a first portion with a main housing defining a longitudinal axis coinciding with the longitudinal axis of the sleeve of the attachment mechanism, wherein the housing of the attachment mechanism may be the main housing or may be attached thereto. The electronic add-on module may further comprise a second portion coupled to the first portion allowing relative axial movement parallel to the longitudinal axis with respect to the first portion. The second portion may be a button partially received in the main housing of the first portion. In an example, the first portion may define an auxiliary dose dial user interface configured to be attached to a dose dial user interface of the drug delivery device, such that the first portion follows the movement of the dose dial user interface and vice versa when attached to the drug delivery device, and the second portion may define an auxiliary injection user interface configured to apply pressure onto an injection user interface of the drug delivery device.

The second portion may be at least partially encased by and retained in the first portion. For example, the first portion has a cavity receiving at least partially the second portion. The second portion may be axially movable relative to the first portion in a restricted manner preventing full disassembly of the first and second portions. In other words, they can be moved a limited distance relative to each other for operating the drug delivery device. A spring may be provided biasing the second portion in the proximal direction with respect to the first portion. In other words, the optional spring may hold the second portion which may be a shuttling button assembly in place while at rest and return it to its neutral position after actuation.

According to an independent aspect of the present disclosure, the second portion may comprise an electrical power source, e.g. a battery or a rechargeable cell, a printed circuit board assembly (PCBA), e.g. comprising and/or forming a control unit, a sensor arrangement, for example an acoustic sensor arrangement comprising e.g. at least one microphone, configured to detect a relative rotational movement between at least two component parts of the drug delivery device, a communication unit for communicating with another device, e.g. for wireless transfer of data, and/or a switch arrangement, e.g. for turning the electronic module on and off and/or for waking the module or its components from a sleeping mode or a low power consumption mode.

An assembly according to the present disclosure comprises a drug delivery device and an electronic add-on module configured for releasable attachment to the drug delivery device.

Preferably, the drug delivery device comprises: a device housing with a container configured to receive a drug or a cartridge filled with a drug, a dose setting unit comprising a dose dial user interface at least rotationally moveable with respect to the device housing during dose setting and an injection user interface at least axially moveable with respect to the device housing for causing dose dispensing, and a dose delivery unit comprising a plunger at least axially moveable with respect to the device housing during dose dispensing.

Although not required in the context of the present disclosure, the drug delivery device may optionally comprise further components such as a drive sleeve, a number sleeve, a clutch, a cap, a needle, a spring, a lead screw or the like, interacting with the dose button, the dose dial grip, the drive sleeve, the plunger and/or the housing, for example as disclosed in WO 2004/078239 A1. However, the present disclosure is not limited to the drug delivery device of WO 2004/078239 A1. Other suitable drug delivery devices to be used with such a module may comprise a dial grip for selecting a variable dose and a separate dose button for initiating or performing dose dispensing, e.g. as described in EP 1 570 876 B1, EP 2 814 547 B1, EP 2 890 434 B1, WO 2009/132777 A1, U.S. Pat. No. 6,663,602 B2, U.S. Pat. No. 7,241,278 B2 or U.S. Pat. No. 9,937,294 B2. In addition, other suitable drug delivery devices to be used with such a module may comprise a single knob forming a dial grip for selecting a variable dose and a dose button for initiating or performing dose dispensing, e.g. as described in WO 2005/018721 A1 or WO 2014/033195 A1. Still further, the drug delivery device may be a spring driven device as described in US 2008/306446 A1 or US 2009/054839 A1.

If the drug delivery device has a similar working principle as in the example of WO 2004/078239 A1, during dose setting components of the drug delivery device may perform the following movements. A housing may be stationary and may be used as a reference system for the further movements of other components. A plunger may be stationary and may be guided in a housing thread. A drive sleeve may be provided rotationally coupled to the dose dial grip during dose setting and rotationally constrained to the housing during dose dispensing. In other words, the drive sleeve may be guided in the housing to perform a purely axial movement during dose dispensing. The drive sleeve may perform a helical movement, i.e. a combined axial and rotational movement, and may be in threaded engagement with the plunger. A dial grip may perform a helical movement. A dose button may be free to rotate but axially constrained to the drive sleeve. For example, the dose button may be axially retained to the drive sleeve by a clutch. An optional clutch may perform a helical movement and may couple a number sleeve to the drive sleeve. An optional clutch spring may perform an axial movement and may be guided in housing splines and may click over clutch teeth. An optional number sleeve may be permanently fixed on the dial grip and may perform a helical movement and may be guided in a housing thread. An optional last dose nut may perform a helical movement on a drive sleeve track of the drive sleeve and may be rotationally constrained to the housing. Hence, the last dose nut may perform axial movement relative to the housing and a helical movement with respect to the drive sleeve.

During dose dispensing components of the drug delivery device may perform the following movements. The housing may remain stationary as a reference system for the further movements of other components. The plunger may perform a helical movement and may be guided in the housing thread. The drive sleeve may perform a pure axial movement and may be in threaded engagement with the plunger. The dose dial grip may perform a helical movement and may be permanently fixed on the number sleeve. The dose button may perform an axial movement if coupled to the drive sleeve and/or the clutch. The optional clutch may perform pure axial movement and may decouple the number sleeve from the drive sleeve. The optional clutch spring may perform pure axial movement and may be rotationally constrained to the clutch due to a pressure applied to the dose button. The optional number sleeve may perform a helical movement and may be guided in the housing thread. The optional last dose nut may maintain its axial position on the drive sleeve track and may be rotationally constrained to the housing.

In an assembly according to the present disclosure, when the module is attached to the dose dial user interface of the drug delivery device, the gripping portion, especially the sleeve, may be elastically biased to abut the dose dial user interface in a form fit and/or friction fit when in its clamping condition where the sleeve has a hyperboloid shape.

According to an independent aspect of the present disclosure, the assembly comprises a drug delivery device having a clicker mechanism generating an acoustic feedback signal during specific use conditions, e.g. at least during dose setting. Such a feedback signal may be detected by the electronic module and the module may determine an amount of dose selected and/or dispensed. For example, the clicker mechanism may generate one clicking sound for every IU dispensed, like e.g. in WO 2004/078239 A1, WO 2014/033195 A1, WO 2005/018721 A1 or EP 1 570 876 B1.

The electronic add-on module may be an electronic dose recording system for determining, storing and/or transmitting data indicative of at least a condition of the drug delivery device or its use. For example, the system may detect if the drug delivery device is switched between a dose setting mode and a dose dispensing mode and vice versa. In addition or as an alternative, the system may detect if a dose is set and/or if a dose is dispensed. Still further, the system may detect the amount of dose selected and/or the amount of dose dispensed. Preferably, the electronic add-on module is configured such that it may be switched from a first state having lower energy consumption into a second state having higher energy consumption. This may be achieved by operation of the electronic add-on module, especially by actuating the microswitch. As an alternative, the module may be provided with a wake up functionality which does not require a separate actuation action. The first state may be a sleeping mode and the second mode may be a detection and/or communication mode. As an alternative, an electronic control unit may issue a command, e.g. a signal, to another unit of the electronic dose recording system such that this unit is switched on or rendered operational.

The electronic add-on module may further comprise a communication unit for communicating with another device, e.g. a wireless communications interface for communicating with another device via a wireless network such as Wi-Fi or Bluetooth, or an interface for a wired communications link, such as a socket for receiving a Universal Serial Bus (USB), mini-USB or micro-USB connector. Preferably, the electronic add-on module comprises an RF, Wi-Fi and/or Bluetooth unit as the communication unit. The communication unit may be provided as a communication interface between the electronic add-on module and the exterior, such as other electronic devices, e.g. mobile phones, personal computers, laptops and so on. For example, dose data may be transmitted by the communication unit to the external device. The dose data may be used for a dose log or dose history established in the external device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about 4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (antidiabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin;

B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N—(ω-carboxyheptadecanoyl)-des(B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Chorion-gonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, deimmunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having crossover binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices of the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding domain immunoglobulin fusion proteins, camelized antibodies, and immunoglobulin single variable domains. Additional examples of antigen-binding antibody fragments are known in the art. The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four chain antibody), or VHH (derived from a heavy chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363: 446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74: 277-302).

For the term "dAb's" and "domain antibody", reference is for example made to Ward et al. 1989 (Nature 341: 544), to Holt et al. 2003 (Trends Biotechnol. 21: 484); as well as to WO 2004/068820, WO 2006/030220, WO 2006/003388. It should also be noted that, although less preferred in the context of the present disclosure because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms "axial", "radial", or "circumferential" as used herein may be used with respect to a first longitudinal axis of the attachment mechanism, its sleeve, electronic add-on module, the first portion, the second portion, the drug delivery device, the cartridge, the housing, the cartridge holder or the assembly of the drug delivery device and the electronic add-on module, e.g. the axis which extends through the proximal and distal ends of the cartridge.

"Distal" is used herein to specify directions, ends or surfaces which are arranged or are to be arranged to face or point towards dispensing end of the electronic add-on module or the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the electronic add-on module or the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example. Similarly, a distal element compared to a proximal element is located closer to the dispensing end than to the proximal end. Furthermore, when the electronic add-on module is considered alone, the term "distal" may be used with regard to the more distal end of the electronic add-on module, which is located closer to the dispensing end of the drug delivery device when attached to the drug delivery device, and the term "proximal" may be used with regard to the proximal end of the electronic add-on module, which is located further away from the dispensing end of the drug delivery device when attached to the drug delivery device.

BRIEF DESCRIPTION OF THE FIGURES

In the following, non-limiting, examples of the attachment mechanism, the electronic add-on module, the drug delivery device and the assembly of the drug delivery device and the electronic add-on module are described in more detail by making reference to the drawings, in which.

DETAILED DESCRIPTION

In the Figures, identical elements and components as well as identical elements and components in different examples or embodiments, i.e. elements and components acting identical or provided for the same purposes but belong to different examples, are provided with the same reference signs.

Figure 1:
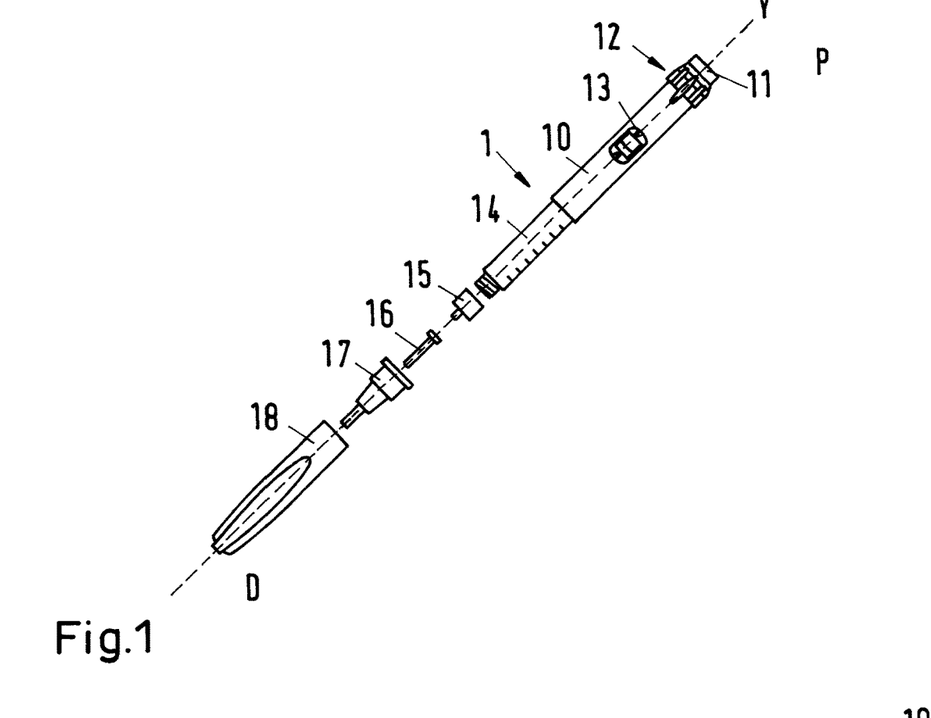
FIG. 1 shows a drug delivery device.

FIG. 1 shows an exploded view of an exemplary medicament or drug delivery device 1. The drug delivery device 1 is a pen-type injector comprising a housing 10 in which a drive mechanism for dose setting and dose dispensing is arranged. The drug delivery device 1 extends from a distal point to a proximal direction P or from a proximal point to a distal direction D along a longitudinal axis Y of the drug delivery device 1. In order to set a dose for delivery a user may rotate or dial a dose dial grip 12 with respect to the housing 10, wherein the dose dial grip 12 is arranged at or near a proximal end of the housing 10. During dose setting the dose dial grip 12 may perform a helical movement, i.e. a combined axial and rotational movement, or may perform pure rotational movement.

The drive mechanism of the drug delivery device 1 may comprise a plunger, a drive sleeve, a clutch, a clutch spring, a number sleeve, a last dose nut and so on, which may move during dose setting and/or dose dispensing. Although not all of these components are shown in detail, for example, the drive mechanisms disclosed in EP 1 570 876, EP 2 814 547, U.S. Pat. No. 9,937,294 B2 or WO 2004/078239 A1 represent suitable drive mechanisms for the present disclosure.

Once the dose is set by means of the dose dial grip 12, the user may press a dose button 11 arranged at the proximal end of the drug delivery device 1 in the distal direction D in order to dispense the dose. When pressing the dose button 11, the user applies a force directed towards the proximal end of the drug delivery device 1, wherein the force moves the dose button 11 in the distal direction of the pen and parallel to the longitudinal axis Y. This axial movement of the dose button 11 releases the drive mechanism for example by decoupling a number sleeve from the drive sleeve, wherein irrespective of which component of the drug delivery device 1 performs a rotational movement during dose delivery, the dose dial grip 12 is coupled to a respective component in order to perform a rotational movement during dose delivery.

Figure 2:
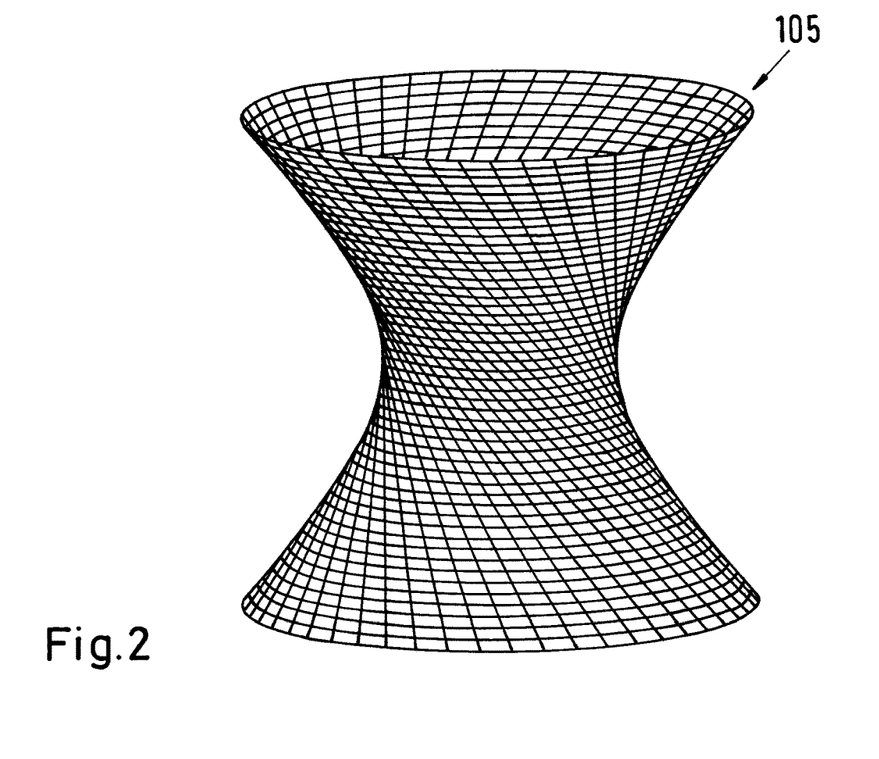
FIG. 2 shows a sleeve elastically deformed into a hyperboloid shape.

This rotational movement of the dose dial grip 12 during dose delivery may be used to determine, for example, the actual dose delivered by means of an electronic add-on module 100 as shown in in FIGS. 2 and 3 and described here below.

The exemplary drug delivery device 1 shown in FIG. 1 comprises in addition to the dose dial grip 12 and the dose button 11 an optional dosage window 13, a container 14, and a needle 15.

The set dose may be displayed via the dosage window 13. The container 14 may be filled directly with a drug, for example insulin, or may be configured to receive a cartridge and thus act as a cartridge holder. The needle 15 may be affixed to the container or the receptacle. During dose dispensing the drug is dispensed through the needle 15. The needle 15 may be protected by an inner needle cap 16. In addition, the needle 15 may be protected by an outer cap 17 and/or a drug delivery device cap 18.

In order for an electronic add-on module 100 to be functionally attached to a drug delivery device 1, i.e. attached and usable, either the drug delivery device 1 can be adapted to the electronic add-on module 100 or, conversely, the electronic add-on module 100 can be adapted to the drug delivery device 1. Regardless of this, the drug delivery device 1 as well as the electronic add-on module 100 may have different examples, wherein the further description with respect to the drug delivery device 1 essentially deals with the dose button 11, the dose dial grip 12 and the drive sleeve inside the housing 10.

Figure 3:
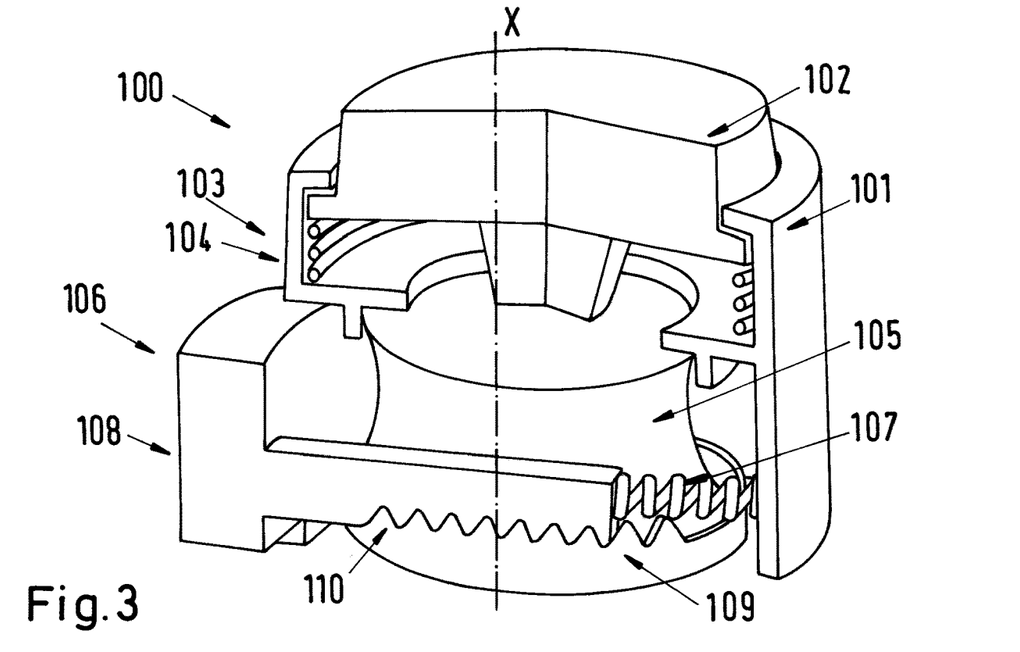
FIG. 3 shows a partially cutaway view of a module with an attachment mechanism according to the present disclosure in its clamping condition.
Figure 4:
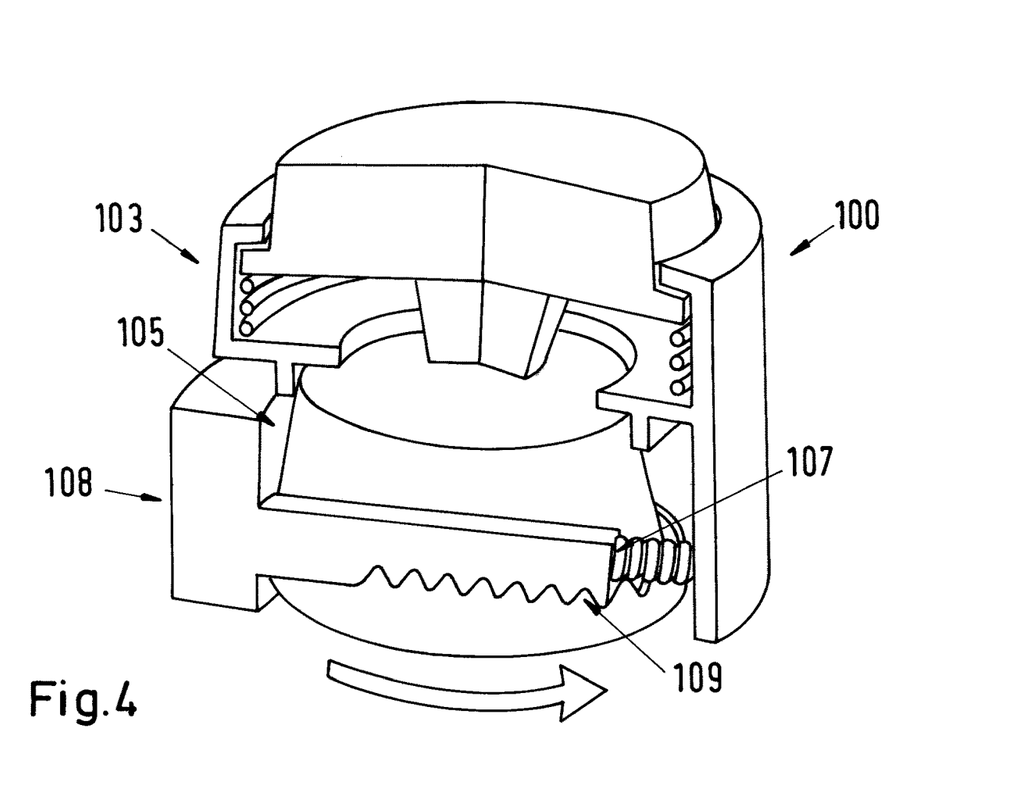
FIG. 4 shows a partially cutaway view of the module of FIG. 3 with the attachment mechanism in its open condition.

FIGS. 3 and 4 show an exemplary embodiment of an electronic add-on module 100 suitable for releasable attachment to a user interface of drug delivery device 1. The module 100 substantially comprises a first portion 101 and a second portion 102 which are coaxially arranged on a first longitudinal axis X coinciding with the longitudinal axis Y of the drug delivery device when attached to each other.

The first portion 101 comprises a main housing 103 receiving the second portion 102. Although not depicted in detail, the second portion 102 may comprise in a button housing a printed circuit board assembly (PCBA), a sensor arrangement, e.g. comprising a microphone, a communication unit and a battery. The main housing 103 is a sleeve-like component with an inwardly protruding, ring-shaped flange at its proximal end which limits axial movement of the second portion 102 in the proximal direction. A spring 104, e.g. a compression spring, is arranged between an inner flange of the first portion and an end face of the second portion, thereby biasing the second portion upwards, i.e. proximally, as seen in FIGS. 3 and 4.

The first portion 101 of the module 100 comprises an attachment mechanism suitable for fastening the module on the drug delivery device 1, especially on the dose dial grip 12. The attachment mechanism comprises the housing 103, a substantially cylindrical or conical sleeve 105 and an actuator 106. The sleeve 105 which forms a gripping portion of the attachment mechanism has a distal end (lower end in FIGS. 3 and 4) and an opposite proximal (upper) end. In the depicted example, the actuator 106 comprises a spring 107, here a compression spring, and an interface 108, here in the form of a push button.

The sleeve 105 is an elastically deformable member, e.g. a flexible elastomeric sleeve. The proximal end of the sleeve 105 is directly or indirectly fixed to the housing 103 such that the proximal end of the sleeve 105 is axially and rotationally constrained to the housing 103 and does not move relative to the housing 103. The distal end of the sleeve 105 is directly or indirectly fixed to a ring 109 such that the distal end of the sleeve 105 is axially and rotationally constrained to the ring 109 and does not move relative to the ring 109. The ring 109 is held and guided within housing 103 such that the ring 109 is rotatable relative to the housing 103. In addition, the ring 109 is held in the housing 103 such that the axial distance between the proximal end of sleeve 105 and the distal end of sleeve 105 does not change, i.e. the sleeve is axially, i.e vertically in the Figures, constrained. The ring 109 and the interface 108 (push button) are coupled to each other by means of meshing teeth 110 such that a movement of the interface 108 e.g. in a direction perpendicular to longitudinal axis X causes a rotation of ring 109 with respect to the housing 103 (as indicated by arrows in FIG. 4).

The attachment mechanism allows the attachment of a module 100 onto the dial grip 12 of an injector pen 1 while adapting to varying geometries and diameters. Bay means of the flexible elastomeric sleeve 105, which is fastened to the housing 103 of the module 100. The attachment mechanism is based on the idea that if the sleeve 105 is twisted while being constrained axially as described above, this relative rotation of the opposite ends of the sleeve 105 causes the initially cylindrical or conical sleeve to deform radially inwards, thereby reducing the inner diameter of the sleeve 105. FIG. 3 depicts the attachment mechanism in a clamping condition or resting state in which the griping portion, i.e. the flexible sleeve 105, is elastically deformed via tension of spring 107 and assumes an hyperboloid shape as shown in FIG. 2.

In its clamping condition, i.e. when the sleeve 105 takes the form of a hyperboloid, the inner diameter of the sleeve 105 is reduced proportional to the rotation angle of the lower ring 109 with respect to the housing 103. If a dial grip 12 or the like component part of a drug delivery device 1 is placed within the sleeve 105 before rotating the ring 109 by means of spring 107, and then the ring 109 is rotated through a sufficient angle, the middle section of the sleeve 105 contracts enough to contact the walls of the dial grip 12 and to grip it securely.

The holding torque depends on the diameter of the dial grip 12 as well as the angle of rotation of the ring 109. The sleeve 105 may be configured to have a holding torque of at least 750 Nmm, e.g. between 1.250 Nmm and 2.500. Nmm or between 1.000 Nmm and 1.500. Nmm, for example about or exactly 1.350 Nmm, when attached to a dial grip 12 or the like component part having a diameter of about 14 mm to 18 mm and when being in its clamping condition, i.e. when the opposite ends of the sleeve 105 are twisted by at least 15° with respect to each other, e.g. by 20° to 50°, for example by about 35°. When the module 100 with its attachment mechanism is at rest, the spring 107 extends and pushes the interface 108 (push button) radially outwards, which causes the ring 109 to rotate. This keeps the sleeve diameter at its minimum point. Due to the elasticity of spring 107, the degree of relative rotation between the opposite ends of the sleeve 105 is not fixed to a single value but may vary in order to adapt the inner diameter of the sleeve to various diameters of different dial grips 12.

In contrast to that, FIG. 4 depicts the attachment mechanism in an open condition or relaxed state of the sleeve 105 having a substantially cylindrical or conical shape. Upon pressing the interface 108 (push button), the ring 109 is turned counterclockwise, which brings the sleeve 105 closer to its neutral, i.e. cylindrical or conical, position, thereby increasing the inner diameter of the closure. In other words, this open condition is caused by pressing the interface 108 of actuator 106 radially inwards against the bias of spring 107 such that the interface 108 rotates ring 109 due to the meshing teeth. The open condition with interface 108 actuated allows either putting the module 100 onto the drug delivery device 1 or to release the module 100 from the drug delivery device 1.

The procedure for using the attachment mechanism is as follows: first, the user attaches the module 100, e.g. a smart cap, onto a suitable drug delivery device 1 by pressing the interface button 108 to unlock the closure and then pressing the module 100 axially onto the dial grip 12 and releasing the interface button 108.

The attachment mechanism can be used to attach an electronic add-on module onto a pen injector dial of any diameter within the design limits. The elastic closure allows smooth adjustment of the inner diameter and gripping force, which makes the mechanism compatible with any arbitrary dial geometry. The friction provided by the elastomeric material of the sleeve 105 pressing against the dial can achieve a good holding torque, meaning that the attachment will not interfere with the basic functionalities of the underlying injector, i.e., dose selection and correction.

REFERENCE NUMERALS

1 drug delivery device
10 housing
11 dose button
12 dose dial grip
13 display window
14 container
15 needle
16 inner needle cap
17 outer cap
18 drug delivery device cap
100 electronic add-on module
101 first portion
102 second portion
103 housing
104 spring
105 sleeve (gripping portion)
106 actuator
107 spring
108 interface (push button)
109 ring
110 teeth
D distal direction
P proximal direction
X longitudinal axis (of the sleeve)
Y longitudinal axis (of the drug delivery device)

The invention claimed is:

1. An attachment mechanism configured to attach a module to an object that is cylindrical or polygonal in cross-section, the attachment mechanism comprising:
   a housing,
   a gripping portion comprising an elastically deformable sleeve with a longitudinal axis, a distal end, and an opposite proximal end which are axially constrained, and
   an actuator for operating the gripping portion between an open condition and a clamping condition,
   wherein the proximal end of the sleeve is coupled to the housing and the distal end of the sleeve is coupled to the actuator, and
   wherein the actuator is configured rotate the distal end and the proximal end of the sleeve relative to each other, thereby operating the gripping portion between the open condition and the clamping condition.

2. The attachment mechanism of claim 1, wherein the proximal end of the sleeve is attached to a ring movable by the actuator.

3. The attachment mechanism of claim 2, wherein the ring is in toothed or splined engagement with the actuator.

4. The attachment mechanism of claim 1, wherein the actuator comprises at least one spring and an interface that can be manipulated by a user.

5. The attachment mechanism of claim 4, wherein the at least one spring is a compression spring acting on the sleeve and the interface is a push button acting on the spring.

6. The attachment mechanism of claim 4, wherein the at least one spring is a torsion spring acting on the sleeve and the interface is a lever acting on the torsion spring.

7. The attachment mechanism of claim 1, wherein the actuator is configured to be displaced in a plane perpendicular to the longitudinal axis of the sleeve or is configured to be rotated about the longitudinal axis of the sleeve, thereby operating the gripping portion between the open condition and the clamping condition.

8. The attachment mechanism according to claim 1, wherein the object is a drug delivery device.

9. An electronic add-on module configured to releasably attach to a drug delivery device, the electronic add-on module comprising:
   a housing,
   a gripping portion comprising an elastically deformable sleeve with a longitudinal axis, a distal end, and an opposite proximal end which are axially constrained, and
   an actuator for operating the gripping portion between an open condition and a clamping condition,
   wherein the proximal end of the sleeve is coupled to the housing and the distal end of the sleeve is coupled to the actuator, and wherein the actuator is configured rotate the distal end and the proximal end of the sleeve relative to each other, thereby operating the gripping portion between the open condition and the clamping condition.

10. The electronic add-on module of claim 9, comprising a first portion defining a longitudinal axis coinciding with the longitudinal axis of the sleeve.

11. The electronic add-on module of claim 9, further comprising a second portion coupled to the first portion and configured to allow relative axial movement parallel to the longitudinal axis with respect to the first portion.

12. The electronic add-on module of claim 11, wherein the first portion defines an auxiliary dose dial user interface configured to be attached to a dose dial user interface of the drug delivery device, such that the first portion follows the movement of the dose dial user interface and vice versa when attached to the drug delivery device, and wherein the second portion defines an auxiliary injection user interface configured to apply pressure onto an injection user interface of the drug delivery device.

13. The electronic add-on module of claim 11, wherein the second portion comprises:
an electrical power source,
a printed circuit board assembly,
a sensor arrangement configured to detect a relative rotational movement between at least two component parts of the drug delivery device,
a communication unit for communicating with another device, and/or
a switch arrangement.

14. The electronic add-on module of claim 13, wherein the second portion comprises the sensor arrangement, and the sensor arrangement is an acoustic sensor arrangement.

15. The electronic add-on module of claim 11, further comprising a spring which biases the second portion in a proximal direction with respect to the first portion.

16. An assembly comprising:
a drug delivery device comprising:
a device housing with a container configured to receive a drug or a cartridge filled with a drug,
a dose setting unit comprising a dose dial user interface at least rotationally moveable with respect to the device housing during dose setting and an injection user interface at least axially moveable with respect to the device housing for causing dose dispensing, and
a dose delivery unit comprising a plunger at least axially moveable with respect to the device housing during dose dispensing; and
an electronic add-on module configured to attach to the drug delivery device, the electronic add-on module comprising:
a housing,
a gripping portion comprising an elastically deformable sleeve with a longitudinal axis, a distal end, and an opposite proximal end which are axially constrained, and
an actuator for operating the gripping portion between an open condition and a clamping condition,
wherein the proximal end of the sleeve is coupled to the housing and the distal end of the sleeve is coupled to the actuator, and
wherein the actuator is configured rotate the distal end and the proximal end of the sleeve relative to each other, thereby operating the gripping portion between the open condition and the clamping condition,
wherein the sleeve of the electronic add-on module is configured to abut the dose dial user interface when the module is attached to the dose dial user interface of the drug delivery device and the gripping portion is in the clamping condition.

17. The assembly of claim 16, wherein the drug delivery device further comprises a clicker mechanism configured to generate an acoustic feedback signal at least during dose setting.

18. The assembly of claim 16, wherein the sleeve of the electronic add-on module is configured to abut the dose dial user interface in a form fit and/or friction fit when the module is attached to the dose dial user interface of the drug delivery device and the gripping portion is in the clamping condition.

19. The assembly of claim 16, wherein the actuator is configured to be displaced in a plane perpendicular to the longitudinal axis of the sleeve or is configured to be rotated about the longitudinal axis of the sleeve, thereby operating the gripping portion between the open condition and the clamping condition.

20. The assembly of claim 16, wherein the actuator comprises at least one spring and an interface that can be manipulated by a user.

* * * * *